(12) United States Patent
Nguyen et al.

(10) Patent No.: US 7,914,544 B2
(45) Date of Patent: *Mar. 29, 2011

(54) MINIMALLY INVASIVE VALVE REPAIR PROCEDURE AND APPARATUS

(75) Inventors: John D. Nguyen, San Jose, CA (US); Laurent Schaller, Los Altos, CA (US); Art Hill, San Francisco, CA (US)

(73) Assignee: Medtronic, Inc., Minneapolis, MN (US)

( * ) Notice: Subject to any disclaimer, the term of this patent is extended or adjusted under 35 U.S.C. 154(b) by 1763 days.

This patent is subject to a terminal disclaimer.

(21) Appl. No.: 11/007,825

(22) Filed: Dec. 7, 2004

(65) Prior Publication Data
US 2005/0101975 A1    May 12, 2005

Related U.S. Application Data

(63) Continuation of application No. 09/686,004, filed on Oct. 10, 2000, now Pat. No. 6,926,730.

(51) Int. Cl.
*A61B 17/08* (2006.01)
(52) U.S. Cl. .................. 606/157; 606/228
(58) Field of Classification Search .......... 606/151, 606/139, 142, 148, 213, 227, 228, 232
See application file for complete search history.

(56) References Cited

U.S. PATENT DOCUMENTS

| | | |
|---|---|---|
| 43,098 A | 6/1864 | Cooper |
| 636,728 A | 11/1899 | Kindel |
| 655,190 A | 8/1900 | Bramson |
| 1,087,186 A | 2/1914 | Scholfield |
| 1,167,014 A | 1/1916 | O'Brien |
| 1,539,221 A | 5/1925 | John |
| 1,583,271 A | 5/1926 | Biro |

(Continued)

FOREIGN PATENT DOCUMENTS

DE    2703529    1/1977

(Continued)

OTHER PUBLICATIONS

Maisano, F. et al. The Double Orifice Technique as a Standardized Approach to Treat Mitral Regurgitation Due to Severe Myxomatous Disease: Surgical Technique (European Journal of Cardiothoracic Surgery, vol. 17 (2000) 201-205).

(Continued)

*Primary Examiner* — Julian W Woo
*Assistant Examiner* — Jing Rui Ou
(74) *Attorney, Agent, or Firm* — Katrina A. Witschen; Mike Jaro

(57) ABSTRACT

A clip of a self-closing type is used for valve repair. The clip is generally U-shaped with two end points separated from each other when constrained to be in an open configuration, but tends to coil up to assume its natural closed configuration if the constraint is removed. At least one end point is connected through a suture to a tissue-penetrating needle. A needle holder has an outer tube and an inner member which has a slit at the front and is slidable inside the outer tube. A double-arm clip assembly with each of the end points of the clip attached through a suture to a separate needle may be used for valve repair and may contain two of such clips mutually connected by a flexible connector whereby two leaflets are held together by the connector, with the two clips each anchored to a corresponding one of the leaflets.

19 Claims, 6 Drawing Sheets

U.S. PATENT DOCUMENTS

| | | | |
|---|---|---|---|
| 1,625,602 A | 4/1927 | Gould et al. | |
| 1,867,624 A | 7/1932 | Hoffman | |
| 2,201,610 A | 5/1940 | Dawson | |
| 2,240,330 A | 4/1941 | Flagg et al. | |
| 2,256,382 A | 9/1941 | Dole | |
| 2,264,679 A | 12/1941 | Ravel | |
| 2,413,142 A | 12/1946 | Jones et al. | |
| 2,430,293 A | 11/1947 | Howells | |
| 2,505,358 A | 4/1950 | Gusberg et al. | |
| 2,516,710 A | 7/1950 | Mascolo | |
| 2,715,486 A | 8/1955 | Marcoff-Moghadam | |
| 2,890,519 A | 6/1959 | Storz, Jr. | |
| 2,940,452 A | 6/1960 | Smialowski | |
| 3,055,689 A | 9/1962 | Jorgensen | |
| 3,057,355 A | 10/1962 | Smialowski | |
| 3,082,426 A | 3/1963 | Miles | |
| 3,143,742 A | 8/1964 | Cromie | |
| 3,150,379 A | 9/1964 | Brown | |
| 3,180,337 A | 4/1965 | Smialowski | |
| 3,249,104 A | 5/1966 | Hohnstein | |
| 3,274,658 A | 9/1966 | Pile | |
| 3,452,742 A | 7/1969 | Muller | |
| 3,506,012 A | 4/1970 | Brown | |
| 3,509,882 A | 5/1970 | Blake | |
| 3,547,103 A | 12/1970 | Cook | |
| 3,570,497 A | 3/1971 | Lemole | |
| 3,608,095 A * | 9/1971 | Barry | 128/898 |
| 3,638,654 A | 2/1972 | Akuba | |
| 3,656,185 A | 4/1972 | Carpentier | |
| RE27,391 E | 6/1972 | Merser | |
| 3,753,438 A | 8/1973 | Wood et al. | |
| 3,762,418 A | 10/1973 | Wasson | |
| 3,776,237 A | 12/1973 | Hill et al. | |
| 3,802,438 A | 4/1974 | Wolvek | |
| 3,825,009 A | 7/1974 | Williams | |
| 3,837,345 A | 9/1974 | Matar | |
| 3,874,388 A | 4/1975 | King et al. | |
| 3,875,648 A | 4/1975 | Bone | |
| 3,905,403 A | 9/1975 | Smith et al. | |
| 3,908,662 A | 9/1975 | Razgulov et al. | |
| 3,910,281 A | 10/1975 | Kletschka et al. | |
| 3,958,576 A | 5/1976 | Komiya | |
| 3,976,079 A | 8/1976 | Samuels | |
| 3,995,619 A | 12/1976 | Glatzer | |
| 4,006,747 A | 2/1977 | Kronenthal et al. | |
| 4,018,228 A | 4/1977 | Goosen | |
| 4,038,725 A | 8/1977 | Keefe | |
| 4,042,979 A | 8/1977 | Angell | |
| 4,073,179 A | 2/1978 | Hickey et al. | |
| 4,103,690 A | 8/1978 | Harris | |
| 4,111,206 A | 9/1978 | Vishnevsky et al. | |
| 4,129,059 A | 12/1978 | Van Eck | |
| 4,140,125 A | 2/1979 | Smith | |
| 4,170,990 A | 10/1979 | Baumgart et al. | |
| 4,185,636 A | 1/1980 | Gabbay et al. | |
| 4,192,315 A | 3/1980 | Hilzinger et al. | |
| 4,214,587 A | 7/1980 | Sakura | |
| 4,217,902 A | 8/1980 | March | |
| 4,243,048 A | 1/1981 | Griffin | |
| 4,324,248 A | 4/1982 | Perlin | |
| 4,345,601 A | 8/1982 | Fukuda | |
| 4,352,358 A | 10/1982 | Angelchik | |
| 4,366,819 A | 1/1983 | Kaster | |
| 4,396,139 A | 8/1983 | Hall et al. | |
| 4,416,266 A | 11/1983 | Baucom | |
| 4,456,017 A | 6/1984 | Miles | |
| 4,465,071 A | 8/1984 | Samuels et al. | |
| 4,470,415 A | 9/1984 | Wozniak | |
| 4,470,533 A | 9/1984 | Schuler | |
| 4,474,181 A | 10/1984 | Schenck | |
| 4,485,816 A | 12/1984 | Krumme | |
| 4,492,229 A | 1/1985 | Grunwald | |
| 4,522,207 A | 6/1985 | Klieman et al. | |
| 4,523,592 A | 6/1985 | Daniel | |
| 4,532,927 A | 8/1985 | Miksza | |
| 4,535,764 A | 8/1985 | Ebert | |
| 4,549,545 A | 10/1985 | Levy | |
| 4,553,542 A | 11/1985 | Schenck et al. | |
| 4,576,605 A | 3/1986 | Kaidash et al. | |
| 4,586,502 A | 5/1986 | Bedi et al. | |
| 4,586,503 A | 5/1986 | Kirsch et al. | |
| 4,593,693 A | 6/1986 | Schenck | |
| 4,595,007 A | 6/1986 | Mericle | |
| 4,612,932 A | 9/1986 | Caspar et al. | |
| 4,622,970 A | 11/1986 | Wozniak | |
| 4,624,255 A | 11/1986 | Schenck et al. | |
| 4,637,380 A | 1/1987 | Orejola | |
| 4,641,652 A | 2/1987 | Hutterer et al. | |
| 4,653,496 A | 3/1987 | Bundy et al. | |
| 4,665,906 A | 5/1987 | Jervis | |
| 4,665,917 A | 5/1987 | Clanton et al. | |
| 4,683,895 A | 8/1987 | Pohndorf | |
| 4,706,362 A | 11/1987 | Strausburg | |
| 4,719,917 A | 1/1988 | Barrows et al. | |
| 4,719,924 A | 1/1988 | Crittenden et al. | |
| 4,730,615 A | 3/1988 | Sutherland et al. | |
| 4,732,151 A | 3/1988 | Jones | |
| 4,809,695 A | 3/1989 | Gwathmey et al. | |
| 4,820,298 A | 4/1989 | Leveen et al. | |
| 4,844,318 A | 7/1989 | Kunreuther | |
| 4,873,975 A | 10/1989 | Walsh et al. | |
| 4,890,615 A | 1/1990 | Caspari et al. | |
| 4,896,668 A | 1/1990 | Popoff et al. | |
| 4,899,744 A | 2/1990 | Fujitsuka et al. | |
| 4,901,721 A * | 2/1990 | Hakki | 606/103 |
| 4,923,461 A | 5/1990 | Caspari et al. | |
| 4,924,866 A | 5/1990 | Yoon | |
| 4,926,860 A | 5/1990 | Stice et al. | |
| 4,929,240 A | 5/1990 | Kirsch et al. | |
| 4,930,674 A | 6/1990 | Barak | |
| 4,932,955 A | 6/1990 | Merz et al. | |
| 4,935,027 A | 6/1990 | Yoon | |
| 4,950,015 A | 8/1990 | Nejib et al. | |
| 4,950,283 A | 8/1990 | Dzubow et al. | |
| 4,950,285 A | 8/1990 | Wilk | |
| 4,957,498 A | 9/1990 | Caspari et al. | |
| 4,983,176 A | 1/1991 | Cushman et al. | |
| 4,990,152 A | 2/1991 | Yoon | |
| 4,991,567 A | 2/1991 | McCuen et al. | |
| 4,994,069 A | 2/1991 | Ritchart et al. | |
| 4,997,439 A | 3/1991 | Chen | |
| 5,002,550 A | 3/1991 | Li | |
| 5,002,562 A | 3/1991 | Oberlander | |
| 5,002,563 A | 3/1991 | Pyka et al. | |
| 5,007,920 A | 4/1991 | Torre | |
| 5,011,481 A | 4/1991 | Myers et al. | |
| 5,020,713 A | 6/1991 | Kunreuther | |
| 5,026,379 A | 6/1991 | Yoon | |
| 5,032,127 A | 7/1991 | Frazee et al. | |
| 5,035,692 A | 7/1991 | Lyon et al. | |
| 5,035,702 A | 7/1991 | Taheri | |
| 5,042,707 A | 8/1991 | Taheri | |
| 5,047,047 A | 9/1991 | Yoon | |
| 5,053,047 A | 10/1991 | Yoon | |
| 5,064,431 A | 11/1991 | Gilbertson et al. | |
| 5,074,874 A * | 12/1991 | Yoon et al. | 606/224 |
| 5,088,692 A | 2/1992 | Weiler | |
| 5,100,418 A | 3/1992 | Yoon | |
| 5,100,421 A | 3/1992 | Christoudias | |
| 5,104,407 A | 4/1992 | Lam et al. | |
| 5,119,983 A | 6/1992 | Green et al. | |
| 5,123,913 A | 6/1992 | Wilk et al. | |
| 5,127,413 A | 7/1992 | Ebert | |
| 5,129,913 A | 7/1992 | Ruppert | |
| 5,152,769 A | 10/1992 | Baber | |
| 5,154,189 A | 10/1992 | Oberlander | |
| 5,158,566 A | 10/1992 | Pianetti | |
| 5,171,250 A | 12/1992 | Yoon | |
| 5,171,252 A | 12/1992 | Friedland | |
| 5,174,087 A | 12/1992 | Bruno | |
| 5,178,634 A | 1/1993 | Ramos Martinez | |
| 5,192,294 A | 3/1993 | Blake | |
| 5,196,022 A | 3/1993 | Bilweis | |
| 5,201,880 A | 4/1993 | Wright et al. | |
| 5,207,694 A | 5/1993 | Broome | |
| 5,217,027 A | 6/1993 | Hermens | |
| 5,219,358 A | 6/1993 | Bendel et al. | |

| | | | | | | |
|---|---|---|---|---|---|---|
| 5,221,259 A | 6/1993 | Weldon et al. | | 5,571,119 A | 11/1996 | Atala |
| 5,222,961 A | 6/1993 | Nakao et al. | | 5,571,175 A | 11/1996 | Vanney et al. |
| 5,222,976 A | 6/1993 | Yoon | | 5,582,616 A | 12/1996 | Bolduc et al. |
| 5,234,447 A | 8/1993 | Kaster et al. | | 5,582,619 A | 12/1996 | Ken |
| 5,236,440 A | 8/1993 | Hlavacek | | 5,584,879 A | 12/1996 | Reimold et al. |
| 5,242,456 A | 9/1993 | Nash et al. | | 5,586,983 A | 12/1996 | Sanders et al. |
| 5,242,457 A | 9/1993 | Akopov et al. | | 5,591,179 A | 1/1997 | Edelstein |
| 5,246,443 A | 9/1993 | Mai | | 5,593,414 A | 1/1997 | Shipp et al. |
| 5,250,053 A | 10/1993 | Snyder | | 5,593,424 A | 1/1997 | Northrup, III |
| 5,258,011 A | 11/1993 | Drews | | 5,597,378 A | 1/1997 | Jervis |
| 5,261,917 A | 11/1993 | Hasson et al. | | 5,601,571 A | 2/1997 | Moss |
| 5,269,783 A | 12/1993 | Sander | | 5,601,572 A | 2/1997 | Middleman et al. |
| 5,269,809 A | 12/1993 | Hayhurst et al. | | 5,601,600 A | 2/1997 | Ton |
| 5,282,825 A | 2/1994 | Muck et al. | | 5,603,718 A | 2/1997 | Xu |
| 5,290,289 A | 3/1994 | Sanders et al. | | 5,609,608 A | 3/1997 | Benett et al. |
| 5,304,117 A | 4/1994 | Wilk | | 5,618,311 A | 4/1997 | Gryskiewicz et al. |
| 5,304,204 A | 4/1994 | Bregen | | 5,628,757 A | 5/1997 | Hasson |
| 5,306,296 A | 4/1994 | Wright et al. | | 5,630,540 A | 5/1997 | Blewett |
| 5,312,436 A | 5/1994 | Coffey et al. | | 5,632,752 A | 5/1997 | Buelna |
| 5,314,468 A | 5/1994 | Ramos Martinez | | 5,632,753 A | 5/1997 | Loeser |
| 5,330,503 A | 7/1994 | Yoon | | 5,643,295 A * | 7/1997 | Yoon .......................... 606/151 |
| 5,334,196 A | 8/1994 | Scott et al. | | 5,643,305 A | 7/1997 | Al-Tameem |
| 5,336,233 A | 8/1994 | Chen | | 5,645,568 A | 7/1997 | Chervitz et al. |
| 5,336,239 A | 8/1994 | Gimpelson | | 5,653,716 A | 8/1997 | Malo et al. |
| 5,346,459 A | 9/1994 | Allen | | 5,653,718 A | 8/1997 | Yoon |
| 5,350,420 A | 9/1994 | Cosgrove et al. | | 5,658,312 A | 8/1997 | Green et al. |
| 5,353,804 A | 10/1994 | Kornberg et al. | | 5,660,186 A | 8/1997 | Bachir |
| 5,355,897 A | 10/1994 | Pietrafitta et al. | | 5,665,109 A | 9/1997 | Yoon |
| 5,356,424 A | 10/1994 | Buzerak et al. | | 5,669,918 A | 9/1997 | Balazs et al. |
| 5,364,406 A | 11/1994 | Sewell | | 5,676,670 A | 10/1997 | Kim |
| 5,366,459 A | 11/1994 | Yoon | | 5,683,417 A * | 11/1997 | Cooper ..................... 606/223 |
| 5,366,462 A | 11/1994 | Kaster et al. | | 5,690,662 A | 11/1997 | Chiu et al. |
| 5,366,479 A | 11/1994 | McGarry et al. | | 5,695,504 A | 12/1997 | Gifford, III et al. |
| 5,374,268 A | 12/1994 | Sander | | 5,695,505 A | 12/1997 | Yoon |
| 5,376,096 A | 12/1994 | Foster | | 5,697,913 A | 12/1997 | Sierocuk et al. |
| 5,382,259 A | 1/1995 | Phelps et al. | | 5,697,943 A | 12/1997 | Sauer et al. |
| 5,383,904 A | 1/1995 | Totakura et al. | | 5,700,270 A | 12/1997 | Peyser et al. |
| 5,387,227 A | 2/1995 | Grice | | 5,700,271 A | 12/1997 | Whitfield et al. |
| 5,403,331 A | 4/1995 | Chesterfield | | 5,702,412 A | 12/1997 | Popov et al. |
| 5,403,333 A | 4/1995 | Kaster | | 5,707,362 A | 1/1998 | Yoon |
| 5,403,338 A | 4/1995 | Milo | | 5,707,380 A | 1/1998 | Hinchliffe et al. |
| 5,403,346 A | 4/1995 | Loeser | | 5,709,693 A | 1/1998 | Taylor |
| 5,413,584 A | 5/1995 | Schulze | | 5,709,695 A | 1/1998 | Northrup, III |
| 5,413,597 A | 5/1995 | Krajicek | | 5,715,987 A | 2/1998 | Kelley et al. |
| 5,417,684 A | 5/1995 | Jackson et al. | | 5,716,370 A | 2/1998 | Williamson, IV et al. |
| 5,417,700 A | 5/1995 | Egan | | 5,720,755 A | 2/1998 | Dakov |
| 5,423,821 A | 6/1995 | Pasque | | 5,725,539 A | 3/1998 | Matern |
| 5,431,666 A | 7/1995 | Sauer et al. | | 5,725,542 A | 3/1998 | Yoon |
| 5,437,680 A | 8/1995 | Yoon | | 5,725,554 A | 3/1998 | Simon et al. |
| 5,437,681 A | 8/1995 | Meade et al. | | 5,728,135 A | 3/1998 | Bregen et al. |
| 5,437,685 A * | 8/1995 | Blasnik .......................... 606/151 | | 5,732,872 A | 3/1998 | Bolduc et al. |
| 5,439,479 A | 8/1995 | Shichman et al. | | 5,735,290 A | 4/1998 | Sterman et al. |
| 5,445,167 A | 8/1995 | Yoon et al. | | 5,746,753 A | 5/1998 | Sullivan et al. |
| 5,445,644 A | 8/1995 | Pietrafitta et al. | | 5,755,778 A | 5/1998 | Kleshinski |
| 5,450,860 A | 9/1995 | O'Connor | | 5,766,189 A | 6/1998 | Matsuno |
| 5,451,231 A | 9/1995 | Rabenau et al. | | 5,769,870 A | 6/1998 | Salahieh et al. |
| 5,452,733 A | 9/1995 | Sterman et al. | | 5,779,718 A | 7/1998 | Green et al. |
| 5,454,834 A | 10/1995 | Boebel et al. | | 5,782,397 A | 7/1998 | Koukline |
| 5,456,246 A | 10/1995 | Schmieding et al. | | 5,782,844 A | 7/1998 | Yoon et al. |
| 5,462,561 A | 10/1995 | Voda | | 5,797,920 A | 8/1998 | Kim |
| 5,474,557 A | 12/1995 | Mai | | 5,797,933 A | 8/1998 | Snow et al. |
| 5,480,405 A | 1/1996 | Yoon | | 5,797,934 A | 8/1998 | Rygaard |
| 5,486,187 A | 1/1996 | Schenck | | 5,797,960 A | 8/1998 | Stevens et al. |
| 5,486,197 A | 1/1996 | Le et al. | | 5,799,661 A | 9/1998 | Boyd et al. |
| 5,488,958 A | 2/1996 | Topel et al. | | 5,799,857 A | 9/1998 | Robertson et al. |
| 5,496,334 A | 3/1996 | Klundt et al. | | 5,810,848 A | 9/1998 | Hayhurst |
| 5,499,990 A | 3/1996 | Schulken et al. | | 5,810,851 A | 9/1998 | Yoon |
| 5,500,000 A | 3/1996 | Feagin et al. | | 5,810,853 A | 9/1998 | Yoon |
| 5,522,884 A | 6/1996 | Wright | | 5,810,882 A | 9/1998 | Bolduc et al. |
| 5,527,342 A | 6/1996 | Pietrzak et al. | | 5,817,113 A | 10/1998 | Gifford, III et al. |
| 5,533,236 A | 7/1996 | Tseng | | 5,820,631 A | 10/1998 | Nobles |
| 5,538,509 A | 7/1996 | Dunlap et al. | | 5,824,002 A | 10/1998 | Gentelia et al. |
| 5,545,214 A | 8/1996 | Stevens | | 5,824,008 A | 10/1998 | Bolduc et al. |
| 5,549,619 A * | 8/1996 | Peters et al. .................. 606/151 | | 5,827,265 A | 10/1998 | Glinsky et al. |
| 5,556,411 A | 9/1996 | Taoda et al. | | 5,827,316 A | 10/1998 | Young et al. |
| 5,562,685 A | 10/1996 | Mollenauer et al. | | 5,830,221 A | 11/1998 | Stein et al. |
| 5,569,205 A | 10/1996 | Hart et al. | | 5,830,222 A | 11/1998 | Makower |
| 5,569,274 A | 10/1996 | Rapacki et al. | | 5,833,698 A | 11/1998 | Hinchliffe |
| 5,569,301 A | 10/1996 | Granger et al. | | 5,849,019 A | 12/1998 | Yoon |

| | | | | | | |
|---|---|---|---|---|---|---|
| 5,851,216 | A | 12/1998 | Allen | 6,143,004 | A | 11/2000 | Davis et al. |
| 5,855,614 | A | 1/1999 | Stevens et al. | 6,149,658 | A | 11/2000 | Gardiner et al. |
| 5,868,702 | A | 2/1999 | Stevens et al. | 6,152,935 | A | 11/2000 | Kammerer et al. |
| 5,868,763 | A | 2/1999 | Spence et al. | 6,152,937 | A | 11/2000 | Peterson et al. |
| 5,871,528 | A | 2/1999 | Camps et al. | 6,159,165 | A | 12/2000 | Ferrera et al. |
| 5,879,371 | A * | 3/1999 | Gardiner et al. ............... 606/224 | 6,159,225 | A | 12/2000 | Makower |
| 5,881,943 | A | 3/1999 | Heck et al. | 6,162,233 | A | 12/2000 | Williamson, IV et al. |
| 5,882,340 | A | 3/1999 | Yoon | 6,165,183 | A | 12/2000 | Kuehn et al. |
| 5,891,130 | A | 4/1999 | Palermo et al. | 6,165,185 | A | 12/2000 | Shennib et al. |
| 5,891,160 | A | 4/1999 | Williamson, IV et al. | 6,171,320 | B1 | 1/2001 | Monassevitch |
| 5,893,369 | A | 4/1999 | LeMole | 6,171,321 | B1 | 1/2001 | Gifford, III et al. |
| 5,893,856 | A | 4/1999 | Jacob et al. | 6,176,413 | B1 | 1/2001 | Heck et al. |
| 5,893,865 | A | 4/1999 | Swindle et al. | 6,176,864 | B1 | 1/2001 | Chapman |
| 5,893,886 | A | 4/1999 | Zegdi et al. | 6,179,840 | B1 | 1/2001 | Bowman |
| 5,895,394 | A | 4/1999 | Kienzle et al. | 6,179,848 | B1 | 1/2001 | Solem |
| 5,904,697 | A | 5/1999 | Gifford, III et al. | 6,179,849 | B1 | 1/2001 | Yencho et al. |
| 5,908,428 | A | 6/1999 | Scirica et al. | 6,183,512 | B1 | 2/2001 | Howanec et al. |
| 5,911,352 | A | 6/1999 | Racenet et al. | 6,190,373 | B1 | 2/2001 | Palermo et al. |
| 5,919,207 | A | 7/1999 | Taheri | 6,193,733 | B1 | 2/2001 | Adams |
| 5,931,842 | A | 8/1999 | Goldsteen et al. | 6,193,734 | B1 | 2/2001 | Bolduc et al. |
| 5,941,434 | A | 8/1999 | Green | 6,197,037 | B1 | 3/2001 | Hair |
| 5,941,442 | A | 8/1999 | Geiste et al. | 6,217,611 | B1 | 4/2001 | Klostermeyer |
| 5,941,888 | A | 8/1999 | Wallace et al. | 6,221,083 | B1 | 4/2001 | Mayer |
| 5,941,908 | A | 8/1999 | Goldsteen et al. | 6,241,738 | B1 | 6/2001 | Dereume |
| 5,944,730 | A | 8/1999 | Nobles et al. | 6,241,741 | B1 | 6/2001 | Duhaylongsod et al. |
| 5,951,576 | A | 9/1999 | Wakabayashi | 6,248,117 | B1 | 6/2001 | Blatter |
| 5,951,600 | A | 9/1999 | Lemelson | 6,250,308 | B1 | 6/2001 | Cox |
| 5,954,732 | A | 9/1999 | Hart et al. | 6,254,615 | B1 | 7/2001 | Bolduc et al. |
| 5,954,735 | A | 9/1999 | Rygaard | 6,269,819 | B1 | 8/2001 | Oz et al. |
| 5,957,363 | A | 9/1999 | Heck | 6,280,460 | B1 | 8/2001 | Bolduc et al. |
| 5,957,938 | A | 9/1999 | Zhu et al. | 6,283,979 | B1 | 9/2001 | Mers Kelly et al. |
| 5,957,940 | A | 9/1999 | Tanner et al. | 6,283,993 | B1 | 9/2001 | Cosgrove et al. |
| 5,961,481 | A | 10/1999 | Sterman et al. | 6,296,622 | B1 | 10/2001 | Kurz et al. |
| 5,961,539 | A | 10/1999 | Northrup, III et al. | 6,296,656 | B1 | 10/2001 | Bolduc et al. |
| 5,964,772 | A | 10/1999 | Bolduc et al. | 6,306,141 | B1 | 10/2001 | Jervis |
| 5,964,782 | A | 10/1999 | Lafontaine et al. | 6,332,893 | B1 | 12/2001 | Mortier et al. |
| 5,972,004 | A | 10/1999 | Williamson, IV et al. | 6,346,074 | B1 | 2/2002 | Roth |
| 5,972,024 | A | 10/1999 | Northrup, III et al. | 6,346,112 | B2 | 2/2002 | Adams |
| 5,976,159 | A | 11/1999 | Bolduc et al. | 6,350,269 | B1 | 2/2002 | Shipp et al. |
| 5,976,161 | A | 11/1999 | Kirsch et al. | 6,352,543 | B1 | 3/2002 | Cole |
| 5,976,164 | A | 11/1999 | Bencini et al. | 6,358,258 | B1 | 3/2002 | Arcia et al. |
| 5,976,178 | A | 11/1999 | Goldsteen et al. | 6,361,559 | B1 | 3/2002 | Houser et al. |
| 5,984,917 | A | 11/1999 | Fleischman et al. | 6,368,348 | B1 | 4/2002 | Gabbay |
| 5,984,959 | A | 11/1999 | Robertson et al. | 6,371,964 | B1 | 4/2002 | Vargas et al. |
| 5,989,242 | A | 11/1999 | Saadat et al. | 6,387,105 | B1 | 5/2002 | Gifford, III et al. |
| 5,989,268 | A | 11/1999 | Pugsley, Jr. et al. | 6,391,038 | B2 | 5/2002 | Vargas et al. |
| 5,989,276 | A | 11/1999 | Houser et al. | 6,402,764 | B1 | 6/2002 | Hendricksen et al. |
| 5,989,278 | A | 11/1999 | Mueller | 6,406,492 | B1 | 6/2002 | Lytle |
| 5,993,465 | A | 11/1999 | Shipp et al. | 6,406,493 | B1 | 6/2002 | Tu et al. |
| 5,993,467 | A * | 11/1999 | Yoon ............................ 606/147 | 6,409,739 | B1 | 6/2002 | Nobles et al. |
| 5,993,468 | A | 11/1999 | Rygaard | 6,409,758 | B2 | 6/2002 | Stobie et al. |
| 5,997,556 | A | 12/1999 | Tanner | 6,416,527 | B1 | 7/2002 | Berg et al. |
| 6,001,110 | A | 12/1999 | Adams | 6,418,597 | B1 | 7/2002 | Deschenes et al. |
| 6,007,544 | A | 12/1999 | Kim | 6,419,658 | B1 | 7/2002 | Restelli et al. |
| 6,010,531 | A | 1/2000 | Donlon et al. | 6,419,681 | B1 | 7/2002 | Vargas et al. |
| 6,013,084 | A | 1/2000 | Ken et al. | 6,419,695 | B1 | 7/2002 | Gabbay |
| 6,022,367 | A | 2/2000 | Sherts | 6,425,900 | B1 | 7/2002 | Knodel et al. |
| 6,024,748 | A | 2/2000 | Manzo et al. | 6,428,550 | B1 | 8/2002 | Vargas et al. |
| 6,032,849 | A | 3/2000 | Mastri et al. | 6,428,555 | B1 | 8/2002 | Koster, Jr. |
| 6,033,419 | A | 3/2000 | Hamblin, Jr. et al. | 6,451,048 | B1 | 9/2002 | Berg et al. |
| 6,036,699 | A | 3/2000 | Andreas et al. | 6,461,320 | B1 | 10/2002 | Yencho et al. |
| 6,036,703 | A | 3/2000 | Evans et al. | 6,475,222 | B1 | 11/2002 | Berg et al. |
| 6,036,710 | A | 3/2000 | McGarry et al. | 6,478,804 | B2 | 11/2002 | Vargas et al. |
| 6,042,607 | A | 3/2000 | Williamson et al. | 6,485,496 | B1 | 11/2002 | Suyker et al. |
| 6,056,751 | A | 5/2000 | Fenton | 6,491,707 | B2 | 12/2002 | Makower et al. |
| 6,063,070 | A | 5/2000 | Eder | 6,497,671 | B2 | 12/2002 | Ferrera et al. |
| 6,066,148 | A | 5/2000 | Rygaard | 6,497,710 | B2 | 12/2002 | Yencho et al. |
| 6,074,401 | A | 6/2000 | Gardiner et al. | 6,514,265 | B2 | 2/2003 | Ho et al. |
| 6,074,418 | A | 6/2000 | Buchanan et al. | 6,517,558 | B2 | 2/2003 | Gittings et al. |
| 6,077,291 | A | 6/2000 | Das | 6,524,338 | B1 | 2/2003 | Gundry |
| 6,080,114 | A | 6/2000 | Russin | 6,533,812 | B2 | 3/2003 | Swanson et al. |
| 6,083,237 | A | 7/2000 | Huitema et al. | 6,537,248 | B2 | 3/2003 | Mulier et al. |
| 6,106,538 | A | 8/2000 | Shiber | 6,537,288 | B2 | 3/2003 | Vargas et al. |
| 6,110,188 | A | 8/2000 | Narciso | 6,547,799 | B2 | 4/2003 | Hess et al. |
| 6,113,611 | A | 9/2000 | Allen et al. | 6,551,332 | B1 | 4/2003 | Nguyen et al. |
| 6,113,612 | A | 9/2000 | Swanson et al. | 6,562,053 | B2 | 5/2003 | Schulze |
| 6,120,524 | A | 9/2000 | Taheri | 6,575,985 | B2 | 6/2003 | Knight et al. |
| 6,132,438 | A | 10/2000 | Fleischman et al. | 6,589,255 | B2 | 7/2003 | Schulze et al. |
| 6,139,540 | A | 10/2000 | Rost et al. | 6,607,541 | B1 | 8/2003 | Gardiner et al. |

| | | |
|---|---|---|
| 6,607,542 B1 | 8/2003 | Wild et al. |
| 6,613,059 B2 | 9/2003 | Schaller et al. |
| 6,629,988 B2 | 10/2003 | Weadock |
| 6,635,214 B2 | 10/2003 | Rapacki et al. |
| 6,641,593 B1 | 11/2003 | Schaller et al. |
| 6,648,900 B2 | 11/2003 | Fleischman et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,541 B1 | 11/2003 | Vargas et al. |
| 6,660,015 B2 | 12/2003 | Berg et al. |
| 6,682,540 B1 | 1/2004 | Sancoff et al. |
| 6,695,859 B1 | 2/2004 | Golden et al. |
| 6,702,826 B2 | 3/2004 | Liddicoat et al. |
| 6,704,401 B2 | 3/2004 | Piepho et al. |
| 6,709,442 B2 | 3/2004 | Miller et al. |
| 6,712,829 B2 | 3/2004 | Schulze |
| 6,719,767 B1 | 4/2004 | Kimblad |
| 6,719,768 B1 | 4/2004 | Cole et al. |
| 6,743,243 B1 | 6/2004 | Roy et al. |
| 6,749,622 B2 | 6/2004 | McGuckin et al. |
| 6,776,782 B2 | 8/2004 | Schulze |
| 6,776,784 B2 | 8/2004 | Ginn |
| 6,776,785 B1 | 8/2004 | Yencho et al. |
| 6,802,847 B1 | 10/2004 | Carson et al. |
| 6,821,286 B1 | 11/2004 | Carranza et al. |
| 6,869,444 B2 | 3/2005 | Gabbay |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,955,679 B1 | 10/2005 | Hendricksen et al. |
| 6,960,221 B2 | 11/2005 | Ho et al. |
| 6,979,337 B2 | 12/2005 | Kato |
| 6,979,338 B1 | 12/2005 | Loshakove et al. |
| 7,022,131 B1 | 4/2006 | Derowe et al. |
| 7,056,330 B2 | 6/2006 | Gayton |
| 7,063,711 B1 | 6/2006 | Loshakove et al. |
| 7,070,618 B2 | 7/2006 | Streeter |
| 7,104,949 B2 | 9/2006 | Anderson et al. |
| 7,182,769 B2 | 2/2007 | Ainsworth et al. |
| 7,220,265 B2 | 5/2007 | Chanduszko et al. |
| 7,220,268 B2 | 5/2007 | Blatter |
| 7,335,212 B2 | 2/2008 | Edoga et al. |
| 7,335,213 B1 | 2/2008 | Hyde et al. |
| RE40,377 E | 6/2008 | Williamson, IV et al. |
| 7,547,313 B2 | 6/2009 | Gardiner et al. |
| 7,556,647 B2 | 7/2009 | Drews et al. |
| 7,722,643 B2 | 5/2010 | Schaller et al. |
| 7,744,611 B2 | 6/2010 | Nguyen et al. |
| 7,763,040 B2 | 7/2010 | Schaller et al. |
| 2001/0018592 A1 | 8/2001 | Schaller et al. |
| 2001/0018593 A1 | 8/2001 | Nguyen et al. |
| 2001/0018611 A1 | 8/2001 | Solem et al. |
| 2001/0021856 A1 | 9/2001 | Bolduc et al. |
| 2001/0047181 A1 | 11/2001 | Ho et al. |
| 2002/0010490 A1 | 1/2002 | Schaller et al. |
| 2002/0042623 A1 | 4/2002 | Blatter et al. |
| 2002/0082614 A1 | 6/2002 | Logan et al. |
| 2002/0099395 A1 | 7/2002 | Acampora et al. |
| 2002/0151916 A1 | 10/2002 | Muramatsu et al. |
| 2002/0165561 A1 | 11/2002 | Ainsworth et al. |
| 2002/0173803 A1 | 11/2002 | Ainsworth et al. |
| 2003/0074012 A1 | 4/2003 | Nguyen et al. |
| 2003/0078603 A1 | 4/2003 | Schaller et al. |
| 2003/0083742 A1 | 5/2003 | Spence et al. |
| 2003/0093118 A1 | 5/2003 | Ho et al. |
| 2003/0120341 A1 | 6/2003 | Shennib et al. |
| 2003/0125755 A1 | 7/2003 | Schaller et al. |
| 2003/0191481 A1 | 10/2003 | Nguyen et al. |
| 2003/0195531 A1 | 10/2003 | Nguyen et al. |
| 2003/0199974 A1 | 10/2003 | Lee et al. |
| 2004/0044406 A1 | 3/2004 | Woolfson et al. |
| 2004/0050393 A1 | 3/2004 | Golden et al. |
| 2004/0068276 A1 | 4/2004 | Golden et al. |
| 2004/0093024 A1 | 5/2004 | Lousararian et al. |
| 2004/0102797 A1 | 5/2004 | Golden et al. |
| 2004/0111099 A1 | 6/2004 | Nguyen et al. |
| 2004/0138685 A1 | 7/2004 | Clague et al. |
| 2004/0167573 A1 | 8/2004 | Williamson et al. |
| 2004/0176663 A1 | 9/2004 | Edoga |
| 2004/0193259 A1 | 9/2004 | Gabbay |
| 2004/0220593 A1 | 11/2004 | Greenhalgh |
| 2005/0004582 A1 | 1/2005 | Edoga |
| 2005/0021054 A1 | 1/2005 | Ainsworth et al. |
| 2005/0043749 A1 | 2/2005 | Breton et al. |
| 2005/0065601 A1 | 3/2005 | Lee et al. |
| 2005/0070924 A1 | 3/2005 | Schaller et al. |
| 2005/0075659 A1 | 4/2005 | Realyvasquez et al. |
| 2005/0075667 A1 | 4/2005 | Schaller et al. |
| 2005/0080454 A1 | 4/2005 | Drews |
| 2005/0101975 A1 | 5/2005 | Nguyen et al. |
| 2005/0107871 A1 | 5/2005 | Realyvasquez et al. |
| 2005/0131429 A1 | 6/2005 | Ho et al. |
| 2005/0267572 A1 | 12/2005 | Schoon et al. |
| 2006/0004389 A1 | 1/2006 | Nguyen et al. |
| 2006/0064118 A1 | 3/2006 | Kimblad |
| 2006/0122634 A1 | 6/2006 | Ino et al. |
| 2006/0253143 A1 | 11/2006 | Edoga |
| 2006/0271081 A1 | 11/2006 | Realyvasquez |
| 2006/0293701 A1 | 12/2006 | Ainsworth et al. |
| 2007/0010835 A1 | 1/2007 | Breton et al. |
| 2007/0027461 A1 | 2/2007 | Gardiner et al. |
| 2007/0106313 A1 | 5/2007 | Golden et al. |
| 2007/0142848 A1 | 6/2007 | Ainsworth et al. |
| 2008/0119875 A1 | 5/2008 | Ino et al. |
| 2008/0255404 A1 | 10/2008 | Nogawa et al. |
| 2009/0036903 A1 | 2/2009 | Ino et al. |
| 2009/0112233 A1 | 4/2009 | Xiao |
| 2009/0264903 A1 | 10/2009 | Lee et al. |
| 2010/0044410 A1 | 2/2010 | Argentine et al. |

FOREIGN PATENT DOCUMENTS

| | | |
|---|---|---|
| DE | 3203410 | 5/1981 |
| DE | 3227984 | 2/1984 |
| DE | 3504202 | 8/1985 |
| DE | 4133800 | 10/1991 |
| DE | 4402058 | 4/1995 |
| DE | 19547617 | 9/1997 |
| DE | 197 11 288 | 10/1998 |
| DE | 19732234 | 1/1999 |
| EP | 0072232 | 2/1983 |
| EP | 0122046 | 3/1983 |
| EP | 0129441 | 12/1984 |
| EP | 0130037 | 1/1985 |
| EP | 0140557 | 5/1985 |
| EP | 0121362 | 9/1987 |
| EP | 0409569 | 1/1991 |
| EP | 0432692 | 6/1991 |
| EP | 0478949 | 8/1991 |
| EP | 0494636 | 7/1992 |
| EP | 0537955 | 4/1993 |
| EP | 0559429 | 9/1993 |
| EP | 0598529 | 5/1994 |
| EP | 0326426 | 12/1994 |
| EP | 0419597 | 12/1994 |
| EP | 0632999 | 1/1995 |
| EP | 0641546 | 3/1995 |
| EP | 0656191 | 6/1995 |
| EP | 0687446 | 12/1995 |
| EP | 0705568 | 4/1996 |
| EP | 0711532 | 5/1996 |
| EP | 0705569 | 10/1996 |
| EP | 0734697 | 10/1996 |
| EP | 0778005 | 6/1997 |
| EP | 0815795 | 1/1998 |
| EP | 0 826 340 | 3/1998 |
| FR | 320 731 | 12/1902 |
| GB | 2223410 | 4/1990 |
| JP | 07308322 | 11/1995 |
| JP | 08336544 | 12/1996 |
| JP | 10337291 | 12/1998 |
| JP | 2009/039556 | 2/2009 |
| RU | 2110222 | 5/1998 |
| SU | 577022 | 10/1977 |
| SU | 1186199 | 10/1985 |
| SU | 1456109 | 2/1989 |

| | | |
|---|---|---|
| SU | 1560133 | 4/1990 |
| WO | 90/06725 | 6/1990 |
| WO | 90/09149 | 8/1990 |
| WO | 90/14795 | 12/1990 |
| WO | 91/07916 | 6/1991 |
| WO | 91/08708 | 6/1991 |
| WO | 91/17712 | 11/1991 |
| WO | 92/05828 | 4/1992 |
| WO | 92/12676 | 8/1992 |
| WO | 92/22041 | 12/1992 |
| WO | 93/01750 | 2/1993 |
| WO | 94/15535 | 7/1994 |
| WO | 94/15537 | 7/1994 |
| WO | 96/00035 | 1/1996 |
| WO | 96/06565 | 3/1996 |
| WO | 96/38090 | 12/1996 |
| WO | 97/12555 | 4/1997 |
| WO | 97/16122 | 5/1997 |
| WO | 97/27898 | 8/1997 |
| WO | 97/28744 | 8/1997 |
| WO | 97/31575 | 9/1997 |
| WO | 97/32526 | 9/1997 |
| WO | 97/40754 | 11/1997 |
| WO | 97/42881 | 11/1997 |
| WO | 98/19636 | 5/1998 |
| WO | 98/30153 | 7/1998 |
| WO | 98/42262 | 10/1998 |
| WO | 98/48707 | 11/1998 |
| WO | 98/52475 | 11/1998 |
| WO | 99/07294 | 2/1999 |
| WO | 99/12484 | 3/1999 |
| WO | 99/15088 | 4/1999 |
| WO | 99/37218 | 7/1999 |
| WO | 99/62408 | 12/1999 |
| WO | 99/62415 | 12/1999 |
| WO | 99/63910 | 12/1999 |
| WO | 99/65409 | 12/1999 |
| WO | WO 99/62406 | 12/1999 |
| WO | WO 99/62409 | 12/1999 |
| WO | WO 00/03759 | 1/2000 |
| WO | 00/15144 | 3/2000 |
| WO | 00/44311 | 8/2000 |
| WO | 00/59380 | 10/2000 |
| WO | 00/60995 | 10/2000 |
| WO | WO 00/64381 | 11/2000 |
| WO | 00/74603 | 12/2000 |
| WO | 01/10310 | 2/2001 |
| WO | 01/19292 | 3/2001 |
| WO | WO 01/26557 | 4/2001 |
| WO | WO 01/26586 | 4/2001 |
| WO | WO 01/28432 | 4/2001 |
| WO | 01/54618 | 8/2001 |
| WO | 01/74254 | 10/2001 |
| WO | 01/82840 | 11/2001 |
| WO | 02/13701 | 2/2002 |
| WO | 02/13702 | 2/2002 |
| WO | 02/30295 | 4/2002 |
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/053289 | 7/2003 |
| WO | 03/088875 | 10/2003 |
| WO | 2004/045378 | 6/2004 |
| WO | 2005/011468 | 2/2005 |
| WO | 2005/041784 | 5/2005 |
| WO | 2005/058170 | 6/2005 |
| WO | 2006/060594 | 6/2006 |
| WO | 2007/067942 | 2/2007 |
| WO | 2009/137517 | 11/2009 |

OTHER PUBLICATIONS

"VCS Clip Applier System," published in 1995 by Auto Suture Company, a Division of U.S. Surgical Corporation.
Emery, et al., Suture Techniques for MIDCAB Surgery, Techniques for Minimally Invasive Direct Coronary Artery Bypass (MIDCAB) Surgery, R.W. Emery ed., Hanley & Belfus, Inc.: Philadelphia, PA, Chapter 12, 1997, pp. 87-91.
Grondin, et al., Carpentier's Annulus and De Vega's Annuloplasty: The end of the tricuspid challenge, Nov. 1975, vol. 70, pp. 852-861.
Holper, et al., Surgery for Tricuspid Insufficiency: Long Term Follow-Up After De Vega Annuloplasty, Thorac Cardiovasc Surgeon, 41, 1993.
Rabago, et al., The New De Vega Technique In Tricuspid Annuloplasty: Results in 150 patients, J. Cardiovas Surg. 1980, 21 pp. 231-238.
Rivera, et al., Carpentier's Flexible Ring Versus De Vega's Annuloplasty, J Thorac Cardiovas Surg, Feb. 1985, 89 pp. 196-203.
Wei, et al., De Vega's Semicircular Annuloplasty For Tricuspid Valve Regurgitation, Ann Thorac Surg, 1993, 55: pp. 482-485.
Wylie, et al., Manual of Vascular Surgery, R. H. Egdahl ed. Spring-Verlag: New York, vol. II, 1986, Table of Contents only.
Wylie, et al., Manual of Vascular Surgery, Springer-Verlag New York, vol. I, 1980, Table of Contents only.
Yun, et al. Mitral Valve Replacement, Mastery of Cardiothoracic Surgery, Lippencott-Raven Publishers, 1998, Chapter 34, pp. 329-341.
International Search Report PCT/US98/00462.
International Search Report PCT/US98/00795.
International Search Report PCT/US98/14211.
International Search Report PCT/US99/12563.
International Search Report PCT/US99/12566.
International Search Report PCT/US00/09092.
International Search Report PCT/US01/10501.
International Search Report PCT/US01/31709.
International Search Report PCT/US01/42653.
International Search Report PCT/US02/10865.
International Search Report PCT/US02/10866.
International Search Report PCT/US02/14261.
International Search Report PCT/US03/12073.
International Preliminary Examination Report PCT/US98/00462.
International Preliminary Examination Report PCT/US98/00795.
International Preliminary Examination Report PCT/US99/12566.
International Preliminary Examination Report PCT/US00/09092.
International Preliminary Examination Report PCT/US01/31709.
International Preliminary Examination Report PCT/US01/42653.
International Preliminary Examination Report PCT/US02/14261.
International Preliminary Examination Report PCT/US02/10865.
International Preliminary Examination Report PCT/US02/10866.
International Preliminary Examination Report PCT/US03/12073.
Written Opinion PCT/US99/12563.
Written Opinion PCT/US99/12566.
Written Opinion PCT/US00/09092.
Written Opinion PCT/US01/10501.
Written Opinion PCT/US01/31709.
Written Opinion PCT/US02/10866.
Written Opinion PCT/US02/14261.
Written Opinion PCT/US03/12073.
International Preliminary Report on Patentability PCT/US2004/023728.
US 6,503,260, 01/2003, Schaller et al. (withdrawn)

* cited by examiner

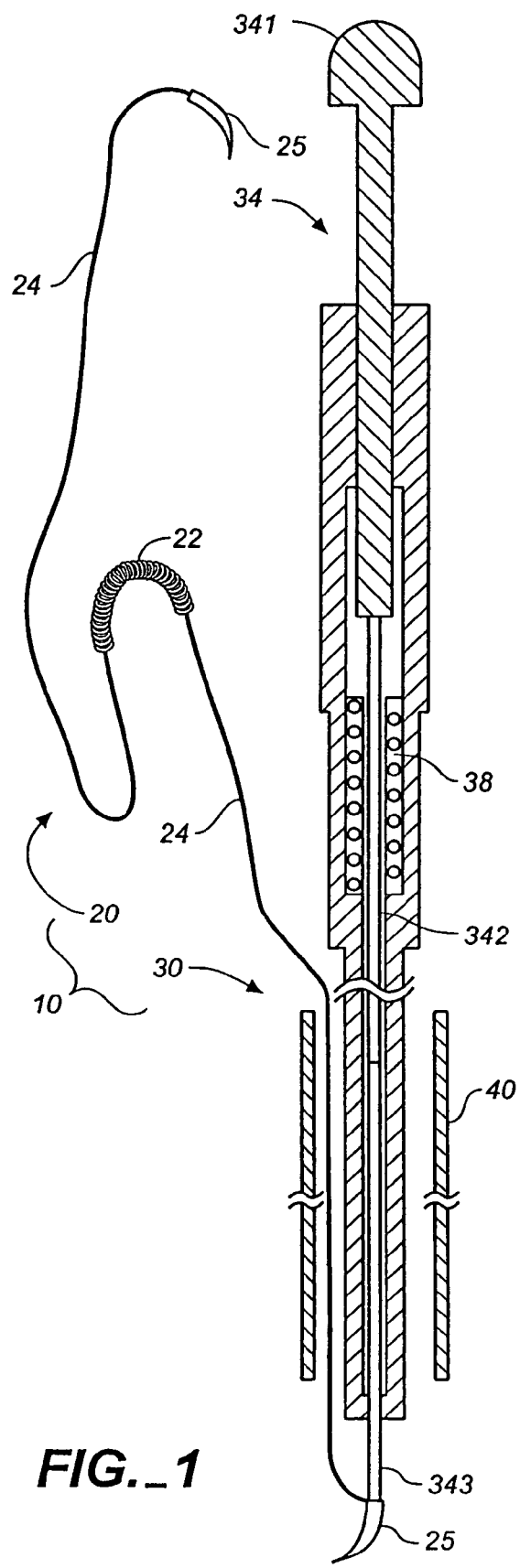
FIG._1

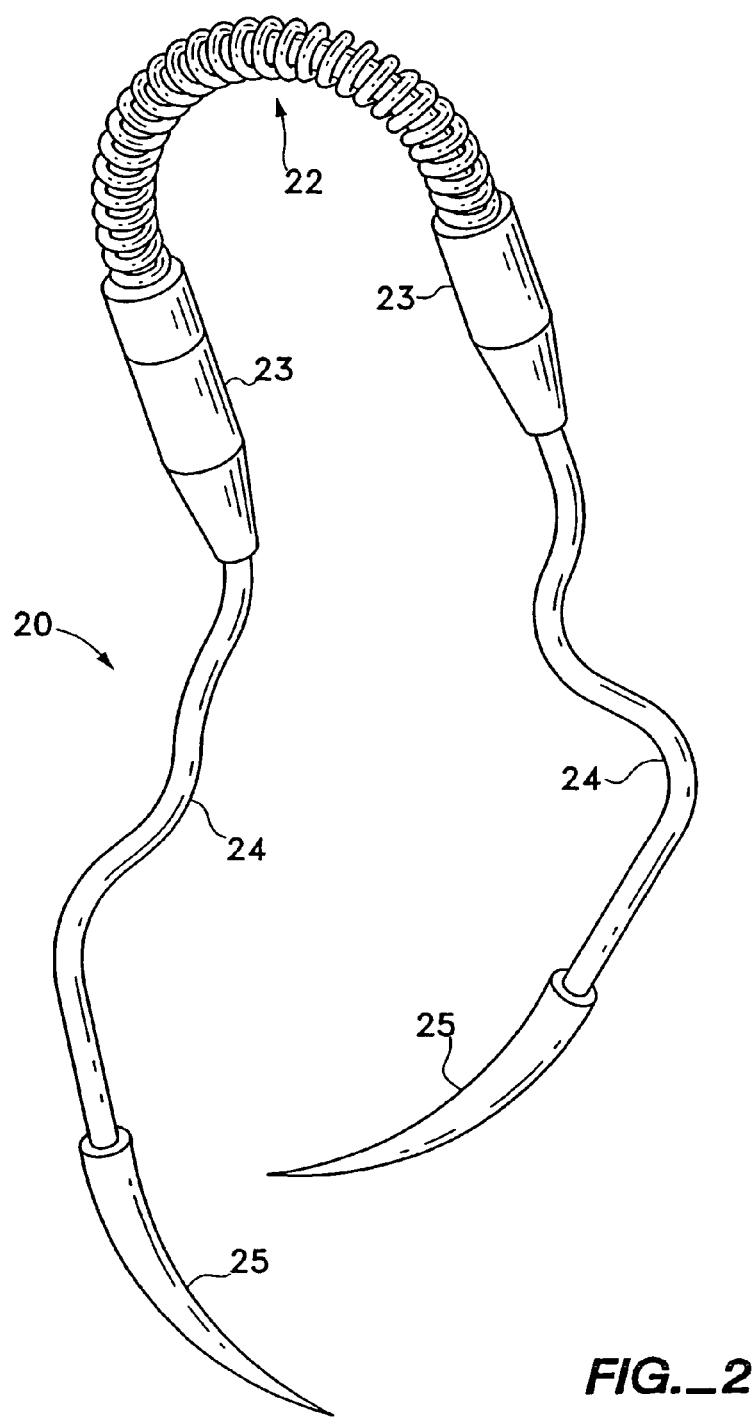
FIG._2

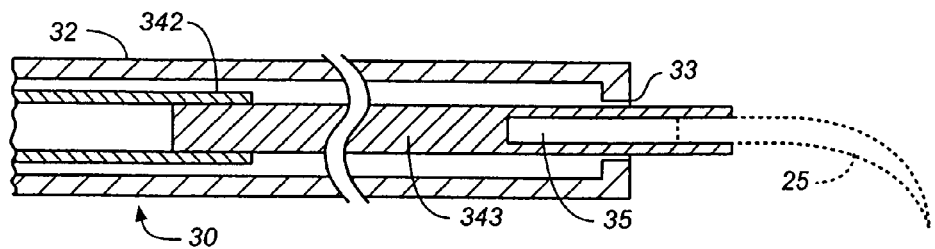
FIG._3
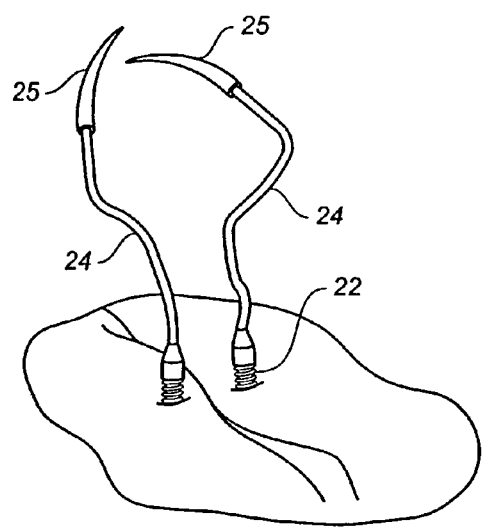
FIG._4A
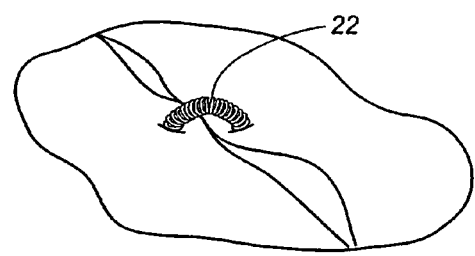
FIG._4B

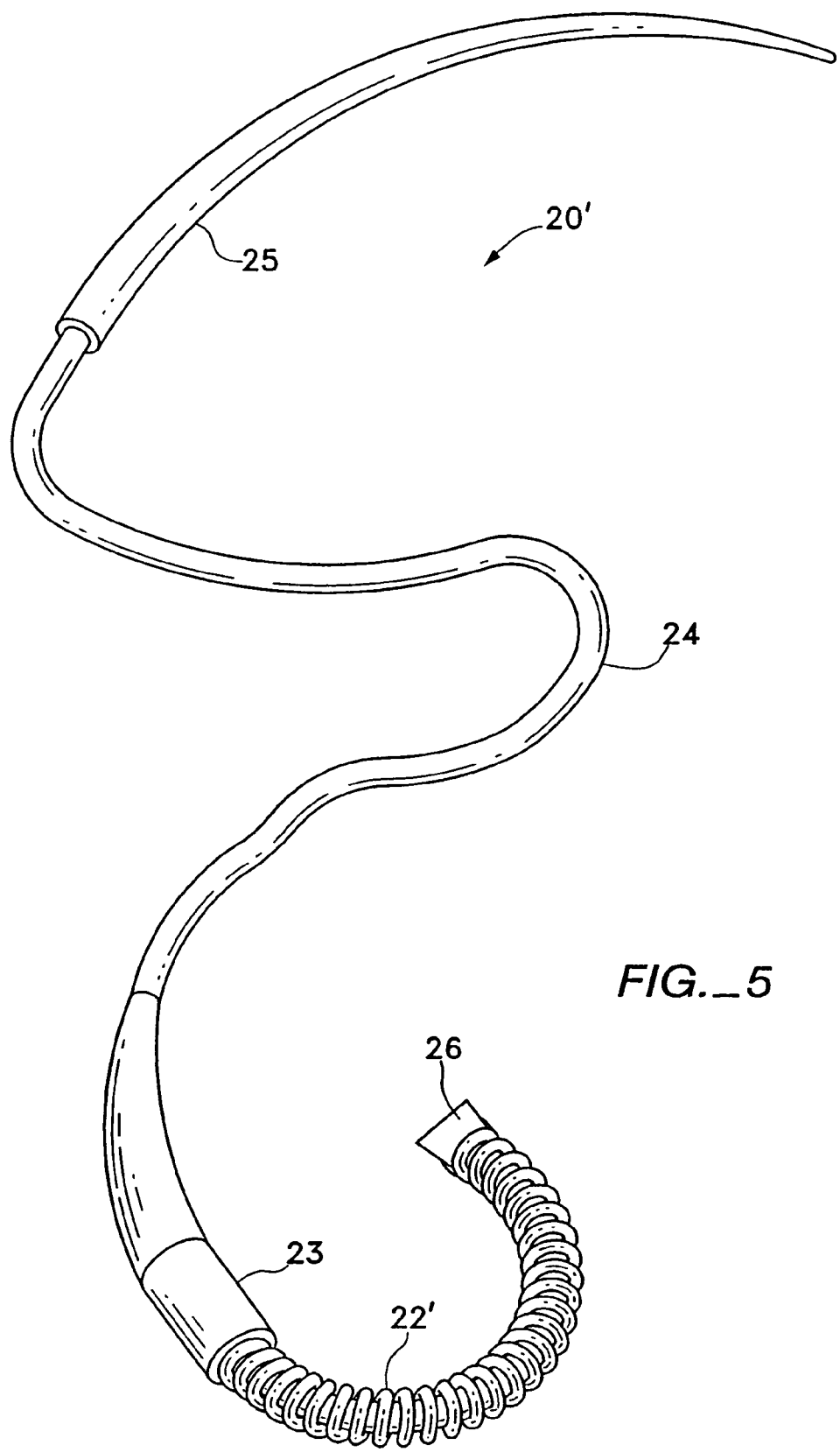
FIG._5

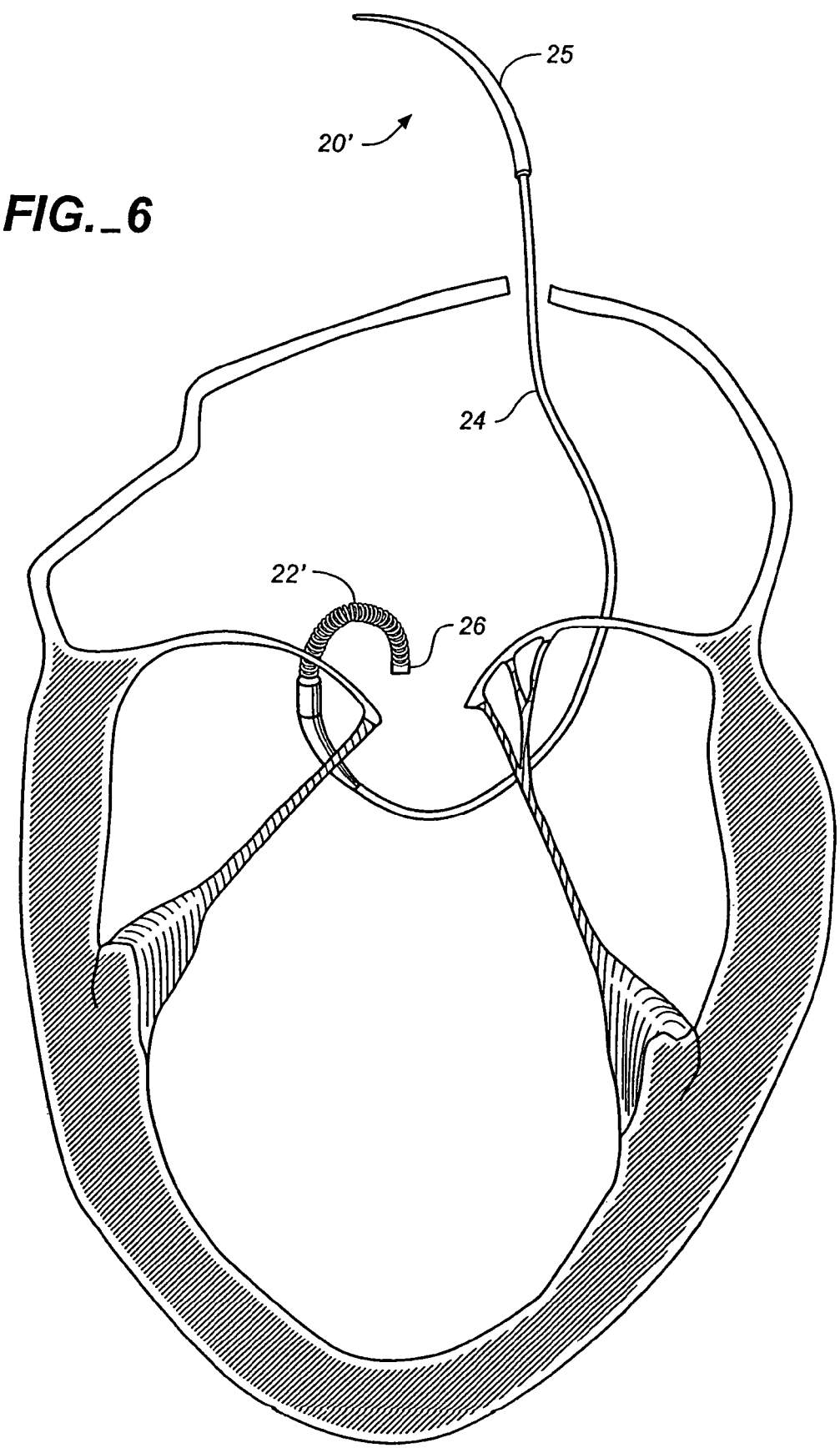
FIG._6

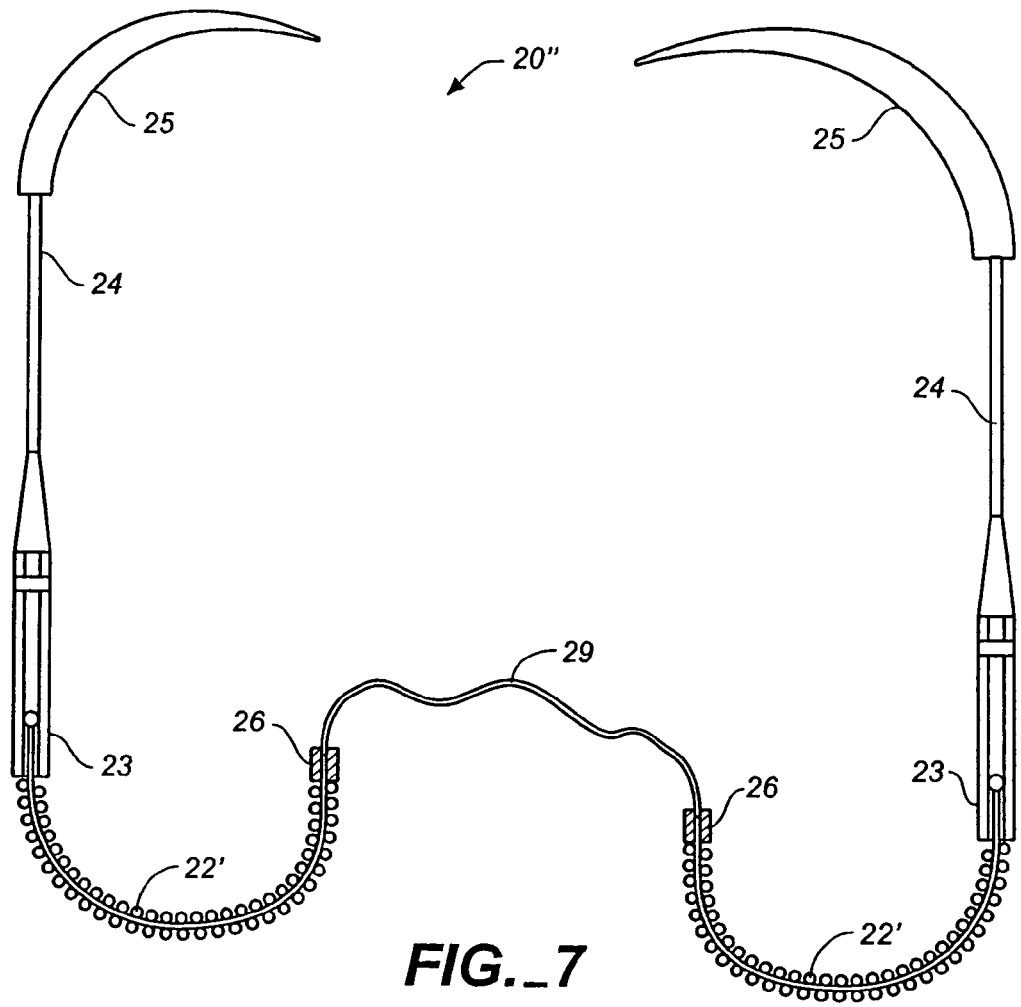
FIG._7
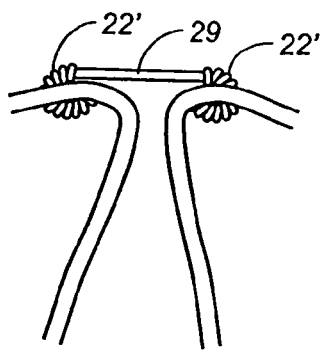
FIG._8A
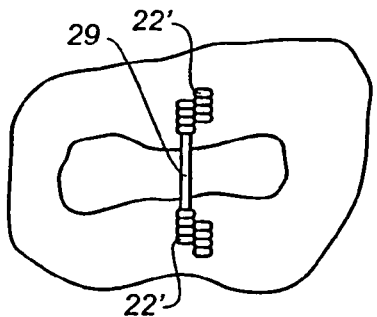
FIG._8B
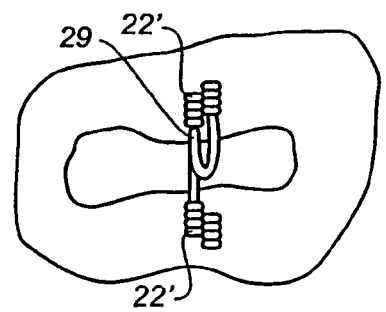
FIG._8C

MINIMALLY INVASIVE VALVE REPAIR PROCEDURE AND APPARATUS

CROSS-REFERENCE TO OTHER APPLICATIONS

This patent application is a continuation of U.S. patent application Ser. No. 09/686,004, filed Oct. 10, 2000, now U.S. Pat. No. 6,926,730 and entitled "Minimally Invasive Valve Repair Procedure And Apparatus."

BACKGROUND OF THE INVENTION

This invention relates to methods and apparatus for minimally invasive valve repair and more particularly to minimally invasive methods and apparatus for reducing the valve orifice.

Valve repair is currently done in open surgical procedures as described, for example, by F. Maisano, et al. in their article entitled "The double-orifice technique as a standardized approach to treat mitral regurgitation due to severe myxomatous disease" which appeared in European Journal of Cardio-thoracic Surgery, Vol. 17 (2000) 201-205. Cumbersome suture management, knot tying, pain and long recovery time are inherent to such open surgical procedures. It now goes without saying that minimally invasive surgery is the preferred procedure, having allowed surgeons to perform procedures with less pain and disability than open surgical procedures. Tissue-connector apparatus and methods usable in such minimally invasive surgery procedures have recently been disclosed in U.S. patent application Ser. Nos. 09/089,884, now U.S. Pat. No. 6,607,541, and 09/090,305 both filed Jun. 3, 1998 and Ser. Nos. 09/259,705, now U.S. Pat. No. 6,514,265, and 09/260,623, now U.S. Pat. No. 6,613,059, both filed Mar. 1, 2000.

It is therefore a general object of this invention to provide improved minimally invasive methods and apparatus for coaptation of leaflets in the case of regurgitation to reduce the annular orifice.

It is a more specific object of this invention to provide such improved minimally invasive methods and apparatus using a tissue-connector apparatus disclosed in aforementioned U.S. patent applications.

SUMMARY OF THE INVENTION

Methods and apparatus embodying this invention with which the above and other objects can be accomplished are characterized as using a clip of a self-closing type as a tissue connector to capture leaflets and secure them together. Such a clip is typically U-shaped, having two end points, when it is constrained to be in an open configuration but is made of a wire of a shape memory material such that it tends to coil up to assume its natural closed configuration. Thus, if such a clip is placed between a pair of valve leaflets to be repaired, having each of its end points penetrating and completely passing through a different one of the leaflets while being constrained to be in its open configuration, and if the constraint which has been keeping the clip in its open configuration is then removed, it naturally tends to coil up, although it will not come to assume its natural closed configuration because it is hooked to the leaflets, tending nevertheless to reduce the distance of separation between its two end points. This has the effect of holding the leaflets together.

Such a clip may be deployed in the form of a clip assembly, having at least one of the end points of the clip connected to a tissue-piecing needle through a flexible member such as a suture and a release mechanism by which the clip can be easily released. The needle is attached to the front end of a needle-holder and passed through a cannula inserted through an incision towards the valve leaflets to be repaired. The needle-holder, according to a preferred embodiment of the invention, is formed with an outer tube and an inner member which is slidable inside the outer tube and is designed such that as the inner member is pushed forward against the biasing force of a spring contained in the outer tube, a slit which is provided at the front end becomes wider for accepting the needle therein but as the inner member is allowed to move to a backward position, the slit becomes narrower and grips the needle tightly.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a schematic view of a tissue-connector apparatus embodying this invention when it is about to be used, its double-arm clip assembly being shown as a diagonal view and its needle holder being shown as a sectional side view;

FIG. 2 is an enlarged external view of the double-arm clip assembly of FIG. 1;

FIG. 3 is an enlarged sectional view of a portion of the needle holder near its front end;

FIG. 4A is a schematic diagonal view of the clip assembly of FIGS. 1 and 2 being used in a valve repair procedure embodying this invention, and FIG. 4B is another schematic diagonal view of the clip of FIG. 4A after it has been released;

FIG. 5 is an external view of a single-arm clip assembly which may be used in a method of minimally invasive valve repair embodying this invention;

FIG. 6 is a schematic sectional view for showing a method of valve repair embodying this invention by using the single-arm clip assembly of FIG. 5;

FIG. 7 is another clip assembly embodying this invention; and

FIG. 8A is a schematic sectional view of leaflets repaired by a clip assembly of FIG. 7, FIG. 8B is a top view of the leaflets of FIG. 8A, and FIG. 8C is a top view of leaflets repaired in an alternative manner.

Throughout herein like components are indicated by the same numerals even where they are components of different assemblies and may not necessarily described repetitiously.

The schematic drawings are intended to be indeed schematic and only to show the basic concepts of the invention, not necessarily representing realistic views, for example, with realistic relative sizes of body components and apparatus components.

DETAILED DESCRIPTION OF THE INVENTION

The invention is described next by way of examples. FIG. 1 shows schematically a tissue-connector apparatus 10 embodying this invention for a minimally invasive procedure. Described briefly, the apparatus 10 consists of a clip assembly 20 and a needle holder 30, which will be described next sequentially in detail.

The clip assembly 20 according to this embodiment may be referred to as the double-arm clip assembly, characterized as having a clip 22 of a self-closing type with two end points each connected through a flexible member 24 such as a suture to a tissue penetrating needle 25 (as disclosed, for example, in aforementioned U.S. patent application Ser. Nos. 09/259, 705, now U.S. Pat. No. 6,514,265, and 09/260,623, now U.S. Pat. No. 6,613,059, both filed Mar. 1, 2000, both of which applications are herein incorporated by reference). Each of the needles 25 has a tissue-piercing sharp point and is connected to a corresponding one of the flexible members 24. As shown more clearly in FIG. 2, the two end points of the clip 22 are each provided with and directly connected to a release mechanism 23 such that it can be released easily from the flexible members 24 and from being constrained to remain in its generally U-shaped open configuration.

The clip 22, or a surgical fastener, of the so-called self-closing type may be one disclosed in aforementioned U.S. patent application Ser. Nos. 09/089,884, now U.S. Pat. No. 6,607,541, and 09/090,305, now U.S. Pat. No. 6,641,593, both filed Jun. 3, 1998 (herein said 09/089,884 and 09/090, 305 applications also incorporated by reference), as well as in aforementioned U.S. patent application Ser. Nos. 09/259, 705, now U.S. Pat. No. 6,514,265, and 09/260,623 now U.S. Pat. No. 6,613,059, characterized as having two end points, being generally U-shaped when in an open configuration (as shown in FIGS. 1 and 2), being naturally in a closed configuration (state or condition) and being elastic (or pseudoelastic, but herein broadly characterized as being "elastic") so as to tend to return to the closed configuration by reducing the separation distance between its end points when forced into an open configuration. As disclosed in aforementioned U.S. patent application Ser. Nos. 09/089,884, now U.S. Pat. No. 6,607,541, and 09/090,305, now U.S. Pat. No. 6,641,593, such a clip 22 may comprise a deformable wire made of a shape memory alloy such as a nickel titanium based alloy (nitinol). It is also known that the alloy may include additional elements, depending on the desired yield strength of the material or the temperature at which particular pseudoelastic or shape transformation characteristics occur. When the clip 22 is in its closed configuration (not shown) with no external restraining force thereupon, it may be in a completely closed loop with its end points in a side-by-side or overlapping orientation, the wire being looped by more than 360°. The diameter of the wire for the clip 22 and the diameter of the loop when it is in the closed configuration may be selected, depending on the application, and do not limit the scope of the invention.

The needle holder 30 consists essentially of a hollow outer tube 32, an inner member 34 and a spring 38, as shown in FIG. 1. The outer tube 32 is elongated, defining a longitudinal direction. The inner member 34 is also longitudinally elongated and is adapted to slide longitudinally inside the outer tube 32 and to releasably grab the needles 25, one at a time. According to the embodiment shown in FIG. 1, the inner member 34 is comprised of a knob 341 at its proximal end, a conjunction tube 342 in the middle and a needle-holding tube 343 in front. The conjunction tube 342 and the needle holding tube 343 are laser-welded together. A threaded adapter is laser-welded to the proximal end of the conjunction tube 342 for allowing the knob 341 to be screwed thereonto after the spring 38 is inserted inside the outer tube 32 such that, once the needle holder 30 is thus assembled, the knob 341, the conjunction tube 342 and the needle-holding tube 343 will move together as a single unit. The front end of the needle-holding tube 343 is provided with a longitudinally elongated slit 35 for holding the needle 25, and the outer tube 32 has a front opening 33, as shown more clearly in FIG. 3. The needle-holding tube 343 with the slit 35 and the front opening 33 of the outer tube 32 are so designed that the slit 35 will open and become sufficiently wide in front as the inner member 34 is pushed forward through the outer tube 32 for accepting a needle 25 (shown by broken lines in FIG. 3) therein and that the opening of the slit 35 tends to become smaller as the inner member 34 is moved backwards through the outer tube 32 so as to retract the needle-holding tube 343 through the front opening 33 of the outer tube 32, causing the needle-holding tube 343 to securely grab the needle 25 once accepted. The spring 38 is disposed inside the outer tube 32 so as to provide a backward biasing force on the inner member 34. In other words, the inner member 34 is normally in a backward position inside the outer tube 32 under the influence of the backward biasing force of the spring 38 thereon. As the user pushes the inner member 34 forward by operating the knob 341 against aforementioned backward biasing force of the spring, the front part of the needle-holding tube 343 protrudes farther outward from the front opening 33 of the outer tube 32 and the slit 35 opens wider, its front opening becoming wide enough to accept the back part of a needle (away from its tissue-piercing sharp point). If the user then releases the force being applied to the knob 341 after the back part of the needle 25 has been accepted inside the slit 35, the backward biasing force by the spring pushes the inner member 34 backward, reducing the length of the needle-holding tube 343 outside the front opening 33 of the outer tube 32. This has the effect of reducing the opening of the slit 35 and hence of having the needle 25 firmly gripped by the needle holder 30. In summary, the user pushes the knob 341 forward to accept the needle 25 and releases the force on the knob 341 to firmly grab it. When a needle is already being held by the needle holder 30, the user has only to push the knob 341 to release it.

A valve repair procedure embodying this invention, such as for reducing the valve orifice by using the apparatus described above, will be described next.

To access a mitral valve, a small incision is made on the appendage of the left atrium. One of the needles 25 of the clip assembly 20 is grabbed by the needle holder 30, as shown in FIG. 1, by pushing the knob 341 forward to accept the needle 25 and then releasing it to firmly attach the needle 25 to the needle holder 30, as described above. A cannula is inserted into the incision. FIG. 1 shows the cannula schematically at 40 but the patient's body part are omitted from FIG. 1. With an aid of an ultrasound machine (not shown), the needle holder 30 is passed through the cannula 40 towards the leaflets, and the needle 25 held by the needle holder 30 is caused to penetrate and be completely pulled through one of the leaflets. Thereafter, the knob 341 is pushed forward to release the needle 25. The knob 341 is pushed forward again to grab the same needle 25 from the other side of the leaflet to secure the needle 25 on the leaflet. Thereafter, the needle 25 is released, the needle holder 30 is pulled out of the cannula 40 and the other of the needles 25 of the double-arm clip assembly 20 is similarly grabbed by its needle holder 30. The same procedure as described above is repeated to cause the second needle 25 of the clip assembly 20 to penetrate and be completely pulled through and be secured to the other of the leaflets. The needles 25 are pulled, together with the flexible members 24 attached thereto, until the clip 22 comes to span the leaflets, as shown in FIG. 4A. Thereafter, the release mechanisms 23 are squeezed by an instrument such as the needle holder 30 itself to release the clip 22 from the flexible members 24. Free of constraints, the clip 22 now tends to return to its natural closed configuration, reducing the distance separating its two end points. This has the effect of tightly bringing the leaflets together, as shown in FIG. 4B, thereby reducing the valve orifice.

The invention was described above by way of only one example but this example is not intended to limit the scope of the invention. Many modifications and variations are possible within the scope of the invention. For example, although the use of a clip assembly having two needles each connected to a corresponding one of the two end points of a generally U-shaped clip was disclosed, use may be made under certain circumstances of a simpler single-arm clip assembly 20' shown in FIG. 5 and described, for example, in aforementioned U.S. patent application Ser. Nos. 09/089,884, now U.S. Pat. No. 6,607,541, and 09/090,305, having only one needle 25 attached through a flexible member 24 and a release mechanism 23 to one of the two end points of a clip 22'. Such a single-arm clip assembly 20' may be used similarly, as described above in connection with the double-arm clip assembly 20 shown in FIGS. 1 and 2, except that the clip 22' is provided with a stopper 26 at the other of its two end points not connected to the flexible member 24 for keeping the clip 22' in its generally U-shaped open configuration. After the needle 25 is caused to penetrate both leaflets, as shown in FIG. 6, the clip 22' can be caused to pull the two leaflets together as the flexible member 24 is pulled, the stopper 26 serving to locate the clip 22' across the leaflets.

FIG. 7 shows still another clip assembly 20" embodying this invention, indicating like components by the same numerals as used in FIGS. 2 and 5. This clip assembly 20" is characterized as having not only two tissue penetrating needles 25 each connected to a flexible member 24 but also two self-closing clips 22' as shown in and explained with reference to FIG. 5, each having a stopper 26 at one end point for keeping the clip 22' in a generally U-shaped open configuration and the other end point being connected to a corresponding one of the flexible members 24 through a release mechanism 23 for separating the clip 22' from the flexible member 24 and thereby releasing the clip 22' from remaining in its open configuration. These two clips 22' are connected through their stoppers 26 by another flexible member 29 which may be a suture or a metal wire.

A clip assembly 22' thus structured may be used in a valve repair procedure, for example, by penetrating a leaflet tissue with one of the needles 25, causing it to come up and out at another position in a manner of ordinary stitching, pulling the associated flexible member 24 until the clip 22' connected thereto penetrates the leaflet tissue partially such that the end point of this clip 22' on the side of the release mechanism 23 penetrates the tissue and reappears on the surface while the other end point on the side of the stopped 26 does not penetrate the tissue, and doing the same with the other needle 25 on the leaflet on the opposite side of the valve opening. After the release mechanisms 23 on both clips 22' are pressed, as described above, to release the clips 22' from the needles 25, each clip 22' tends to coil up, getting firmly attached to the respective leaflet, the flexible member 29 therebetween holding the leaflets together, as shown in FIGS. 8A and 8B. In other words, it is the flexible member 29 between the two clips 22' that holds the leaflets together. As an alternative procedure, the needles 25 may be operated such that the connecting flexible member 29 makes a loop between the leaflets, as shown in FIG. 8C.

Although the clips 22 and 22', when constrained to an open configuration before they are released from the flexible member 24, are described as being generally U-shaped, this description is intended to be interpreted broadly. As should be clear from the intended function of the clips 22 and 22', their open configuration may look more like a C or a J than a U. The release mechanisms 23, described above as serving to release the connection between the clip 22 or 22' and the flexible members 24 and to release the clip 22 or 22' from its forced open configuration, may be structured as disclosed in aforementioned U.S. patent application Ser. No. 09/260,623, now U.S. Pat. No. 6,613,059, but their structure is not intended to limit the scope of the invention.

In summary, the disclosure is intended to be interpreted broadly. Although the invention has been described as being addressed to a method and an apparatus for valve repair, a person skilled in the art will immediately realize that the method and apparatus of this invention as described above can be used for holding two tissue parts close together, not being limited to valve leaflets. The scope of this invention, therefore, is to be understood as including methods of and apparatus for holding two tissue parts close together.

What is claimed is:

1. Apparatus for minimally invasive valve repair, the apparatus comprising:
   a tissue penetrating needle, a flexible member, and a clip, the tissue penetrating needle being connected through the flexible member to the clip, the clip having two end points which are separated from each other when the clip is in an open configuration and tending to return to a naturally closed configuration by reducing distance between the end points when in the open configuration;
   a needle holder including an outer tube and an inner member which has a front end adapted to grab the needle and is slidable inside the outer tube;
   a release mechanism attached to one of the end points of the clip to releasably connect the flexible member to the clip.

2. The apparatus of claim 1 wherein the clip is generally U-shaped when in the open configuration.

3. The apparatus of claim 1 wherein the clip comprises a wire made of shape memory material.

4. The apparatus of claim 1 wherein the clip in the closed configuration is looped by more than 360°.

5. Apparatus for minimally invasive valve repair, the apparatus comprising:
   a tissue penetrating needle, a flexible member, and a clip, the tissue penetrating needle being connected through the flexible member to the clip, the clip having two end points which are separated from each other when the clip is in an open configuration and tending to return to a naturally closed configuration by reducing distance between the end points when in the open configuration;
   a needle holder including an outer tube and an inner member which has a front end adapted to grab the needle and is slidable inside the outer tube, the needle holder further including a spring which is disposed inside the outer tube and serves to apply a biasing force on the inner member backward away from the front end; and
   a release mechanism attached to one of the end points of the clip to releasably connect the flexible member to the clip.

6. The apparatus of claim 5 wherein the front end of the inner member has a slit for accepting and grabbing the needle therein.

7. The apparatus of claim 6 wherein the outer tube, the inner member and the slit are designed such that the slit opens wide enough to accept the needle therein and to release the needle therefrom when the inner member is pushed forward against the biasing force and the slit becomes narrower and firmly grips the needle therein when the inner member is moved backward.

8. The apparatus of claim 5 wherein the clip is generally U-shaped when in the open configuration.

9. The apparatus of claim 5 wherein the clip comprises a wire made of shape memory material.

10. The apparatus of claim 5 including a second needle and a second flexible member coupled to the second needle, wherein each flexible member is connected to one of the two end points of the clip.

11. The apparatus of claim 10 including a second release mechanism to releasably connect the second flexible member to the clip.

12. Apparatus for minimally invasive valve repair, the apparatus comprising:
   a tissue penetrating needle, a flexible member, and a clip, the tissue penetrating needle being connected through the flexible member to the clip, the clip having a first end point and a second end point which are separated from each other when the clip is in an open configuration and tending to return to a naturally closed configuration by reducing distance between the end points when in the open configuration, wherein the clip in the closed configuration is looped by more than 360°; and
   a needle holder including an outer tube and an inner member which has a front end adapted to grab the needle and is slidable inside the outer tube; and
   a release mechanism attached to the first end point of the clip to releasably connect the flexible member to the clip.

13. The apparatus of claim 12 wherein the needle holder further includes a spring which is disposed inside the outer tube and serves to apply a biasing force on the inner member backward away from the front end.

14. The apparatus of claim 13 wherein the front end of the inner member has a slit for accepting and grabbing the needle therein.

15. The apparatus of claim 14 wherein the outer tube, the inner member and the slit are designed such that the slit opens wide enough to accept the needle therein and to release the needle therefrom when the inner member is pushed forward against the biasing force and the slit becomes narrower and firmly grips the needle therein when the inner member is moved backward.

16. The apparatus of claim 12 wherein the clip is generally U-shaped when in the open configuration.

17. The apparatus of claim 12 wherein the clip comprises a wire made of shape memory material.

18. The apparatus of claim 12 including a second needle and a second flexible member coupled to the second needle, wherein each flexible member is connected to one of the two end points of the clip.

19. The apparatus of claim 18 including a second release mechanism attached to the second end point of the clip to releasably connect the second flexible member to the clip.

* * * * *